United States Patent
Kim

(10) Patent No.: US 9,498,301 B2
(45) Date of Patent: Nov. 22, 2016

(54) METHOD FOR MANUFACTURING TRANSPARENT BRACES

(75) Inventor: Tae-Weon Kim, Seoul (KR)

(73) Assignee: E-CLEAR INTERNATIONAL CO., LTD., Seoul (KR)

( * ) Notice: Subject to any disclaimer, the term of this patent is extended or adjusted under 35 U.S.C. 154(b) by 468 days.

(21) Appl. No.: 14/126,443

(22) PCT Filed: Jun. 12, 2012

(86) PCT No.: PCT/KR2012/004622
§ 371 (c)(1),
(2), (4) Date: Dec. 16, 2013

(87) PCT Pub. No.: WO2012/173367
PCT Pub. Date: Dec. 20, 2012

(65) Prior Publication Data
US 2014/0124968 A1    May 8, 2014

(30) Foreign Application Priority Data

Jun. 16, 2011  (KR) .................. 10-2011-0058440
Jul. 11, 2011  (KR) .................. 10-2011-0068445

(51) Int. Cl.
*A61C 7/00*    (2006.01)
*A61C 7/08*    (2006.01)
*A61C 13/00*   (2006.01)

(52) U.S. Cl.
CPC ............... *A61C 7/002* (2013.01); *A61C 7/08* (2013.01); *A61C 13/0019* (2013.01)

(58) Field of Classification Search
CPC ................................ A61C 7/002; A61C 7/08
See application file for complete search history.

(56) References Cited

U.S. PATENT DOCUMENTS

| | | | | |
|---|---|---|---|---|
| 2002/0055081 A1* | 5/2002 | Hughes | ............ | A61C 7/00 433/24 |
| 2008/0050692 A1* | 2/2008 | Hilliard | ............ | A61C 7/08 433/24 |
| 2010/0036682 A1* | 2/2010 | Trosien | ............ | G06Q 10/10 705/3 |

FOREIGN PATENT DOCUMENTS

| | | |
|---|---|---|
| JP | 2005-304904 A | 11/2005 |
| JP | 2010-501258 A | 1/2010 |
| KR | 10-2005-0107520 A | 11/2005 |
| KR | 10-2010-0013822 A | 2/2010 |

OTHER PUBLICATIONS

International Search Report in International Application No. PCT/KR2012/004622, dated Nov. 30, 2012.

* cited by examiner

*Primary Examiner* — Stella Yi
(74) *Attorney, Agent, or Firm* — Park, Kim & Suh, LLC

(57) ABSTRACT

The present invention relates, in general, to a method for manufacturing transparent braces. More particularly, the present invention relates to a method for manufacturing transparent braces in such a way that a plurality of dental molds are manufactured based on orthodontic dental data that is created on the basis of current dental data of a patient and instructions of a dentist and includes a plurality of orthodontic process steps, and then transparent substances are vacuum-pressed onto the respective dental molds.

9 Claims, 22 Drawing Sheets

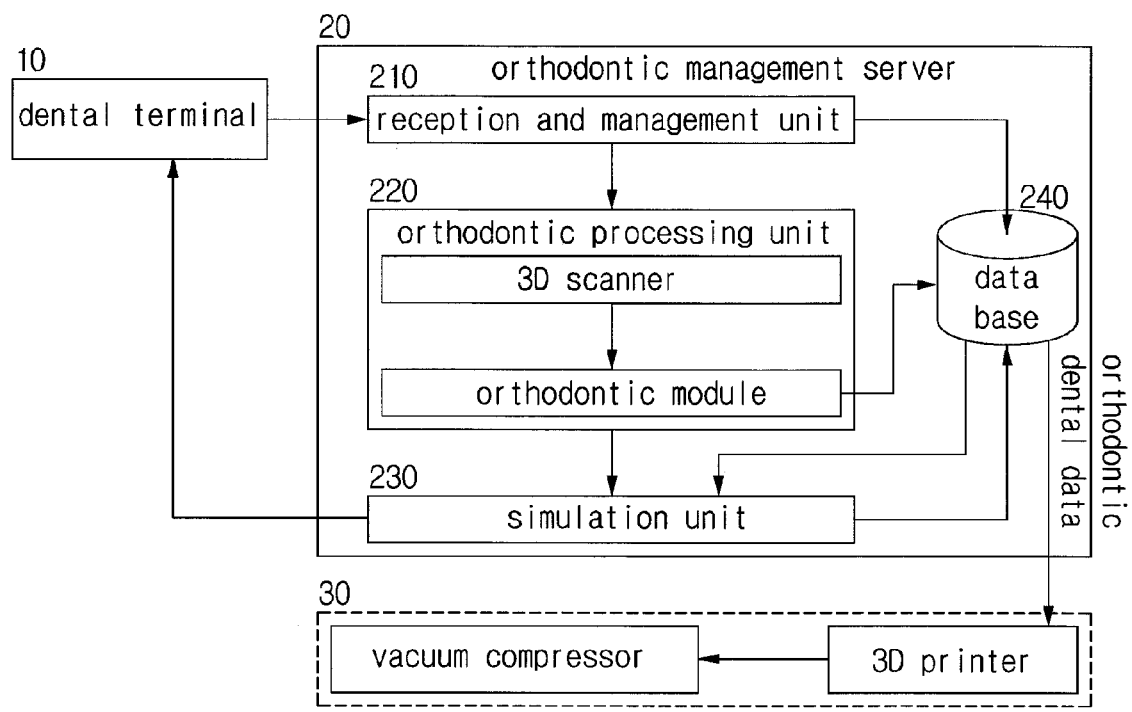

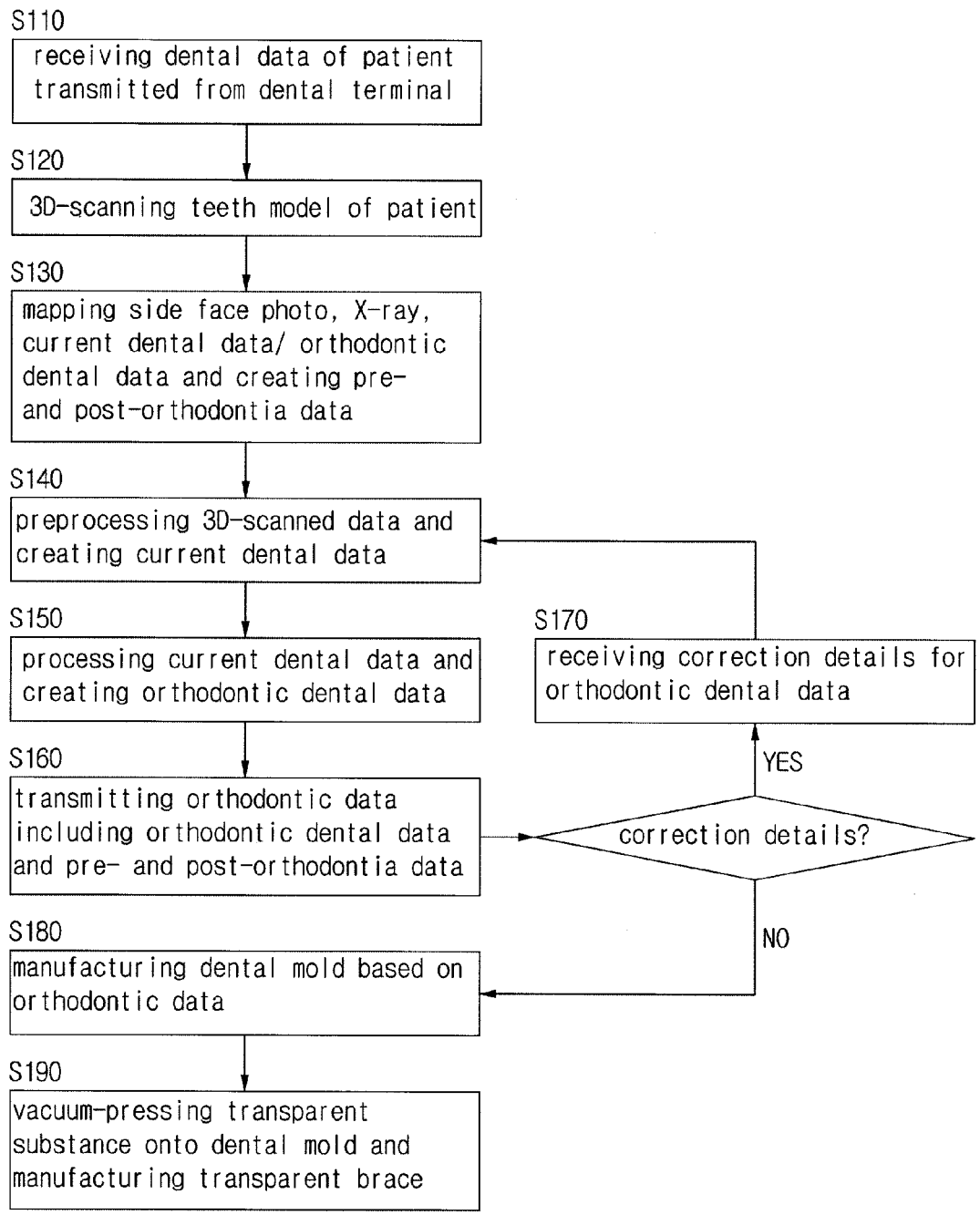

FIG. 3

| Send new case | |
|---|---|
| ▸Patient Name | [Input patient name. ex.) Hong Gil-dong] |
| ▸Date of birth | [Input date of birth of patient. ex.) 19910101] |
| ▸Sex | ○Male ○Female |
| ▸Orthodontic tooth selection | Upper jaw: ☐all ☐18 ☐17 ☐16 ☐15 ☐14 ☐13 ☐12 ☐11 \| ☐21 ☐22 ☐23 ☐24 ☐25 ☐26 ☐27 ☐28<br>Lower jaw: ☐all ☐48 ☐47 ☐46 ☐45 ☐44 ☐43 ☐42 ☐41 \| ☐31 ☐32 ☐33 ☐34 ☐35 ☐36 ☐37 ☐38<br>Select No. of orthodontic tooth |
| ▸Stripping? | ○YES ○NO ○as you want |
| ▸Additional items | Check Item name / cost / Item description<br>☐ Retainer / 10,000 / Retainer for prevention of recurrence after orthodontia (Wearing required for orthodontic treatment duration)<br>☐ Suspender / 10,000 / Device for Intrusion<br>☐ Cow-catch / 10,000 / Device for extrusion<br>☐ Pontic / 5,000 / Artificial tooth for aesthetic supplementation of tooth defect |
| ▸Comments | Input requirements or specialties when manufacturing Clgner |
| ▸Analysis | Side photo : [_____] [Search...]<br>Side X-ray : [_____] [Search...]<br>Front photo : [_____] [Search...]<br>Front X-ray : [_____] [Search...]<br>Upload both photo. and X-ray for analysis |

[OK] [Cancel]

METHOD FOR MANUFACTURING TRANSPARENT BRACES

CROSS-REFERENCE TO RELATED APPLICATIONS

This application is the National Stage filing under 35 U.S.C. 371 of International Application No. PCT/KR2012/004622, filed on Jun. 12, 2012, which claims the benefit of Korean Patent Application No. 10-2011-0058440, filed on Jun. 16, 2011, and Korean Patent Application No. 10-2011-0068445, filed on Jul. 11, 2011, the contents of which are all hereby incorporated by reference herein in their entirety.

TECHNICAL FIELD

The present invention relates, in general, to methods for manufacturing transparent braces and, more particularly, to a method for manufacturing transparent braces in such a way that a plurality of dental molds are manufactured based on orthodontic dental data that is created on the basis of current dental data of a patient and instructions of a dentist and includes a plurality orthodontic process steps, and then transparent substances are vacuum-pressed onto the respective dental molds.

BACKGROUND ART

Generally, orthodontic methods are classified into a metal orthodontic method using an orthodontic device including a metal bracket, a lingual orthodontic method in which an orthodontic device is installed on inner surfaces of the teeth of a patient, and a transparent orthodontic method in which a transparent brace made of transparent material is mounted to the teeth of the patient.

Particularly, in the case of the transparent orthodontic method, the transparent brace made of transparent material is installed on the teeth in such a way that it covers the teeth in a manner similar to that of a mouthpiece. The brace is not easily visible. In addition, the brace is removable and wearable. Therefore, the transparent orthodontic method is receiving much attention, compared to the other orthodontic methods.

The conventional transparent orthodontic method includes obtaining current dental data of a patient, predicting final orthodontic dental data, comparing the current dental data and the orthodontic dental data with each other by morphing so that orthodontic dental data with regard to respective several steps is created, and manufacturing transparent braces for respective steps.

However, in the conventional transparent orthodontic method, the process is divided into several steps only by morphing without taking into consideration a movable range or position of a corresponding tooth. Thus, there is a problem in that a comparatively large error is caused in the orthodontic process.

Moreover, the conventional transparent orthodontic method provides only orthodontic dental data without providing information about the face contour to be predicted after the orthodontia. Thus, it is impossible to verify effects of orthodontia in advance.

DISCLOSURE

Technical Problem

Accordingly, the present invention has been made keeping in mind the above problems occurring in the prior art, and an object of the present invention is to provide a method for manufacturing transparent braces in such a way that orthodontic dental data including a plurality of processing steps is created by expanding, rotating and retracting a tooth in consideration of individual tooth movement, the orthodontic dental data is corrected by mapping it with an X-ray photograph and a side face photograph of a patient so that pre-orthodontia and post-orthodontia data is created with regard to variation in the face contour of the patient and is verified, and then transparent braces are manufactured based on the verified orthodontic dental data.

Technical Solution

In order to accomplish the above object, the present invention provides a method for manufacturing a transparent brace, including: receiving dental data of a patient transmitted from a dental terminal; preprocessing data about a 3D-scanned dental model and creating current dental data of the patient; processing the current dental data through an orthodontia process and creating orthodontic dental data including a plurality of steps; manufacturing a plurality of dental molds in response to the steps through 3D printing based on the orthodontic dental data including the steps; and manufacturing a plurality of transparent braces in response to the steps in such a way transparent substances are vacuum-pressed onto the respective dental molds.

Furthermore, preprocessing the 3D-scanned dental model data may include automatically setting a resolution and a size of the 3D-scanned data to a preset format.

Further, creating the orthodontic dental data may include: dividing teeth of the patient into upper jaw teeth and lower jaw teeth; positioning the current dental data for orthodontia; separating the teeth from a gum area; separating the teeth from each other to secure space for moving a tooth; setting reference teeth information; and processing the tooth based on the set reference teeth information through at least one of an expansion operation, a rotation operation and a retraction operation and creating orthodontic dental data including a plurality of steps.

In addition, creating the pre-orthodontia and post-orthodontia data may include: overlapping a side face photograph of the dental data of the patient with an X-ray photograph of the face of the patient; creating profile information in which reference points of a craniofacial skeleton of the patient are connected to each other while the side face photograph overlaps with the X-ray photograph, and mapping the current dental data with the profile information; changing, from the pre-orthodontia data in which the side face photograph, the X-ray photograph and the current dental data of the patient are mapped with each other, the current dental data to the processed orthodontic dental data; and creating the post-orthodontia data in such a way that, in response to a displacement resulting from the change of the current dental data to the orthodontic dental data, the X-ray photograph and the side face photograph that are integrally mapped with each other are varied by the displacement.

Preferably, verifying the pre-orthodontia and post-orthodontia data may include: transmitting orthodontic data including both the created orthodontic dental data and the pre-orthodontia and post-orthodontia data to the dental terminal, and allowing a dentist and the patient to verify the orthodontic data; filing correction details of the orthodontic data to an orthodontic management server, the dentist determining whether the correction details are present; and feeding back to creating the orthodontic dental data when the correction details are received.

Furthermore, manufacturing the plurality of transparent braces may include vacuum-pressing transparent substances having different thicknesses onto the respective dental molds for the steps and manufacturing the transparent braces having different rigidities in response to the respective steps.

Advantageous Effects

In a method for manufacturing transparent braces according to the present invention, because orthodontic dental data including a plurality of processing steps is created based on individual tooth movement, the orthodontic process can be precisely performed.

Furthermore, the orthodontic dental data is mapped with a face photograph and an X-ray photograph of a patient so that prediction of variation in the face contour of the patient after the orthodontia is possible. Therefore, effects of the orthodontia can be checked in advanced.

In addition, a plurality of transparent braces having different rigidities in response to the respective steps of the orthodontic dental data are manufactured, thus minimizing inconvenience of the patient, and enhancing compatibility with the teeth of the patient, thereby improving the orthodontic effects. Moreover, because the duration for which the patient wears each transparent brace is reduced, there are advantages in terms of hygiene.

DESCRIPTION OF DRAWINGS

FIG. 1 is a block diagram of illustrating a system for manufacturing transparent braces according to a preferred embodiment of the present invention;

FIG. 2 is a flowchart showing a method of manufacturing the transparent brace according to the preferred embodiment of the present invention;

FIG. 3 illustrates dental data of a patient which is transmitted from a dental terminal according to the preferred embodiment of the present invention;

BEST MODE

Figure 4:
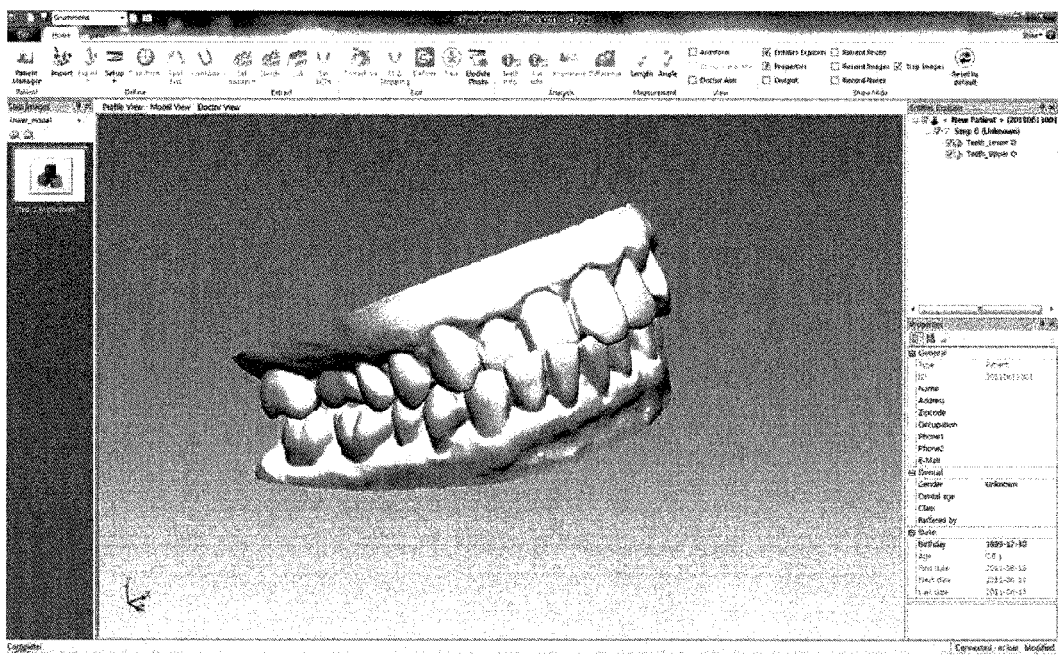
FIGS. 4 through 11 are views showing a process of setting dental data to create orthodontic dental data according to the preferred embodiment of the present invention.

Hereinafter, an embodiment of the present invention will be explained in detail with reference to the attached drawings.

FIG. 1 is a block diagram of illustrating a system for manufacturing transparent braces according to a preferred embodiment of the present invention.

Referring to FIG. 1, the transparent brace manufacturing system according to the present invention includes a dental terminal 10 which transmits dental data of a patient, an orthodontic management server 20 which receives dental data of the patient from the dental terminal and creates orthodontic dental data for the patient through an operation of 3D-scanning and orthodontically-processing the current dental data of the patient, and a brace manufacturing apparatus 30 which manufactures a transparent brace based on the orthodontic dental data created by the orthodontic management server.

The dental terminal 10 is installed in each dental clinic and functions to transmit dental data of the patient. The dental data of the patient includes all data related to the teeth of the patient, for example, a dental X-ray photograph of the patient, front and side face photographs of the patient, orthodontic instructions made by a patient's dentist, a teeth model of the patient, etc.

The dental terminal 10 includes a dental data input program which makes out dental data of the patient and transmits the dental data to the orthodontic management server 20.

The orthodontic management server 20 includes: a reception and management unit 210 which receives the dental data of patients from dental terminals; an orthodontic processing unit 220 which three-dimensionally scans the teeth model of the received dental data of each patient, creates current dental data, preprocesses the current dental data, and creates orthodontic dental data that is processed in consideration of orthodontic instructions of the dentist if the orthodontic instructions are present; a simulation unit 230 which predicts variation in the face contour of the patient resulting from the orthodontia by means of mapping among the created orthodontic dental data, the X-ray photograph and the face photograph of the patient; and a database 240.

The reception and management unit 210 functions to classify dental data of patents transmitted from the dental terminals by dental clinics and patients and receive the classified data. Here, the reception and management unit 210 verifies connection from each dental clinic in such a way an ID and passwords for each dental clinic are previously set and the dental clinic logs in when needed.

The orthodontic processing unit 220 includes a 3D scanner 221 which three-dimensionally scans the teeth model of the patient of the received dental data, and an orthodontic module 222 which preprocesses the current dental data of the patient which is three-dimensionally scanned, processes the current dental data in consideration of orthodontic instructions of the patient's dentist, and creates orthodontic dental data.

Here, in the case where the dental data includes current dental data of the patient which has been three-dimensionally scanned, the orthodontic processing unit may not include the construction of the 3D scanner.

The orthodontic module 222 preprocesses the 3D-scanned current dental data of the patient in such a way as to automatically set it to preset resolution and size. Further, the orthodontic module 222 divides the teeth into upper jaw teeth and lower jaw teeth, positions the current dental data for orthodontia, separates the teeth from the gum area, separates teeth from each other to ensure space for moving the teeth, sets reference teeth information, and expands, rotates and retracts the teeth, thus creating processed orthodontic dental data.

The orthodontic dental data is classified into a plurality of operations according to movement of teeth including expansion, rotation and retraction of the teeth. In other words, expansion, rotation and retraction operations for creating the orthodontic dental data that is an end product form one process. In this way, the orthodontic dental data which is classified into a plurality of operations can be obtained.

Here, teeth expansion, rotation and retraction operations are set such that teeth movement distance is 1 mm or less in each operation The orthodontic module 222 includes a software program for preprocessing teeth and processing orthodontia so that the teeth preprocessing operation and the orthodontic processing operation can be automatically or manually conducted.

The simulation unit 230 maps the side face photograph of the patient, the X-ray photograph and the current dental condition data before the orthodontic processing operation to obtain the conditions of the patient before the orthodontia, maps the patient, the X-ray photograph and the orthodontic dental data created from the orthodontic processing unit, and outputs the contour variation to be predicted after the orthodontia.

The brace manufacturing apparatus 30 includes a 3D-printer 310 which manufactures a brace mold based on the created orthodontic dental data, and a vacuum compressor 320 which vacuum-presses a transparent substance onto the brace mold manufactured by the 3D printer, thus manufacturing a transparent brace.

Here, the transparent material must be nontoxic biocompatible material in consideration of the fact that it is installed in the mouth. For instance, Tupan which is transparent biocompatible material, may be used as the transparent material.

Hereinafter, a method of manufacturing the transparent brace according to the embodiment of the present invention will be described.

FIG. 2 is a flowchart showing the method of manufacturing the transparent brace according to the embodiment of the present invention.

Referring to FIG. 2, the transparent brace manufacturing method includes receiving dental data of a patient that is transmitted from a dental terminal (at step S110).

The dentist of the corresponding dental clinic can access the orthodontic management server in such a way as to input ID/passwords if the dentist is registered as a member. If the dentist is not registered, the access is possible after member registration via inputting personal information and ID/passwords.

Here, the personal information may include information, such as the name of the dentist, the name and address of the dental clinic, etc., which specifies the dental clinic.

The dental data of the patient must basically include a teeth model of the patient. As shown in FIG. 3, the dental data can be accepted to the reception and management unit in the shape of a data format including the instructions of the dentist and information about X-ray photographs, front photographs and side face photographs of the patient to compare pre-orthodontia with post-orthodontia.

After the dental data of the patient is received from the dental terminal, the teeth model of the patient is scanned by means of the 3D scanner (at step S120).

Thereafter, as shown in FIG. 4, the orthodontic module obtains the current dental data of the patient through preprocessing (at step S130).

Here, the preprocessing refers to a process of automatically set the resolution and size of the 3D-scanned data to preset conditions.

Subsequently, the orthodontic module orthodontically-processes the current dental data, thus creating orthodontic dental data (at step S140).

In detail, from the current dental data, the teeth are divided into the upper jaw teeth and the lower jaw teeth.

Figure 5:
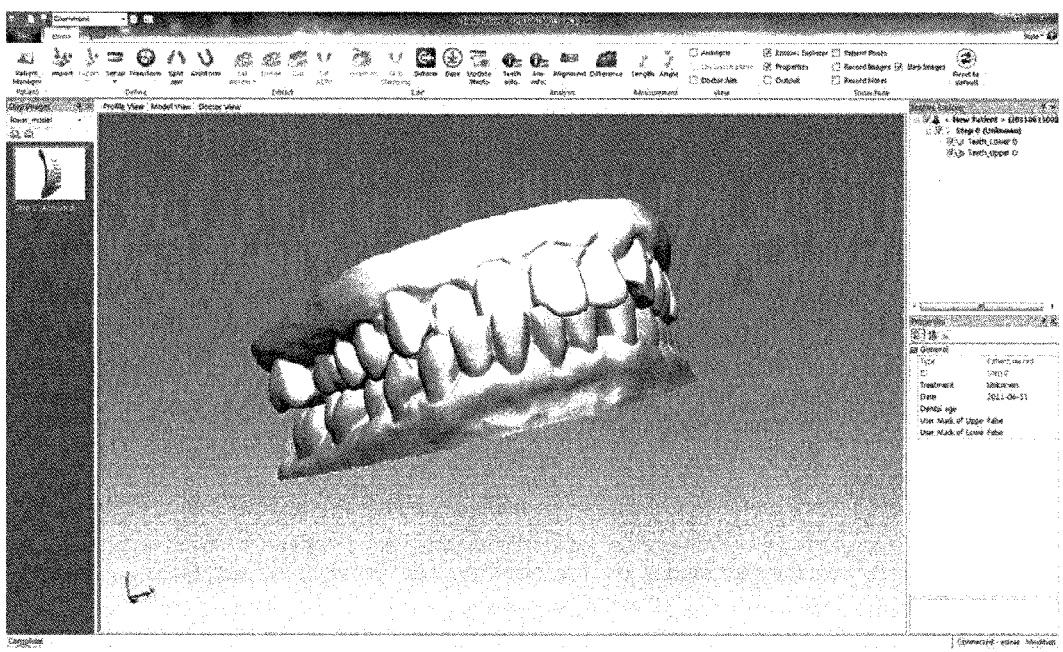

Basically, because the teeth are divided into the upper jaw area and the lower jaw area, it is necessary to divide the teeth into the upper jaw teeth and the lower jaw teeth for movement of individual teeth. As shown in FIG. 5, the upper jaw teeth and the lower jaw teeth are distinguished by detecting an image of a boundary between the upper jaw teeth and the lower jaw teeth or selective designation.

The current dental data in which the teeth are divided into the upper jaw teeth and the lower jaw teeth is positioned.

Figure 6:
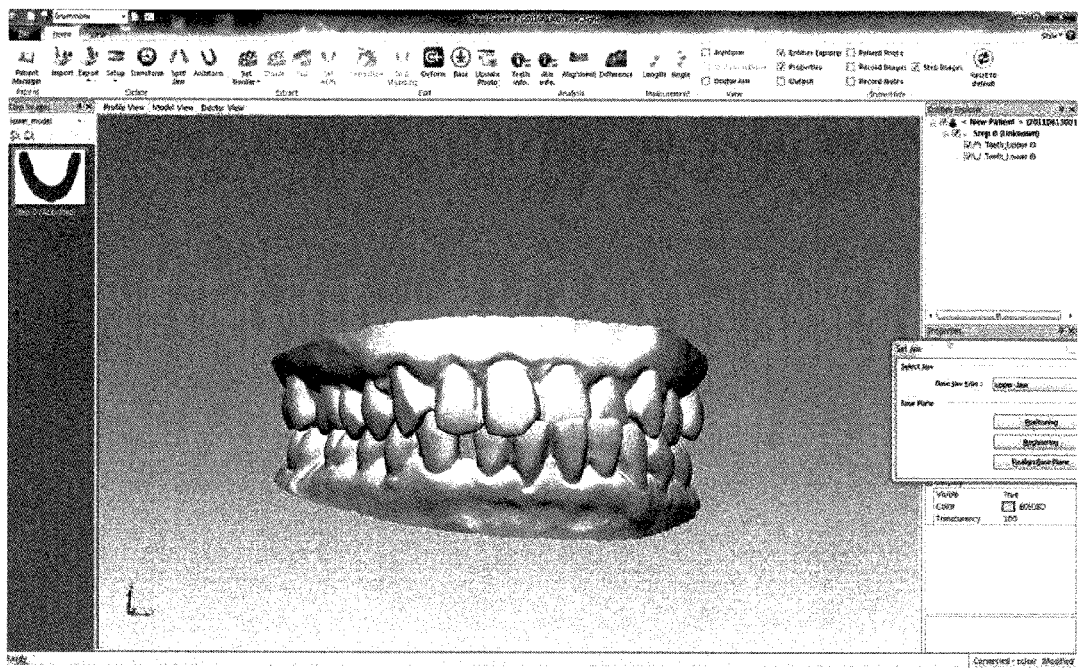

That is, with regard to the current scanned dental data, when the teeth are scanned in a state of being inclined at a predetermined angle, the positioning operation is required for correct position alignment of the teeth, as shown in FIG. 6.

Thereafter, the orthodontic module separates the teeth and the gum area from each other.

Figure 7:
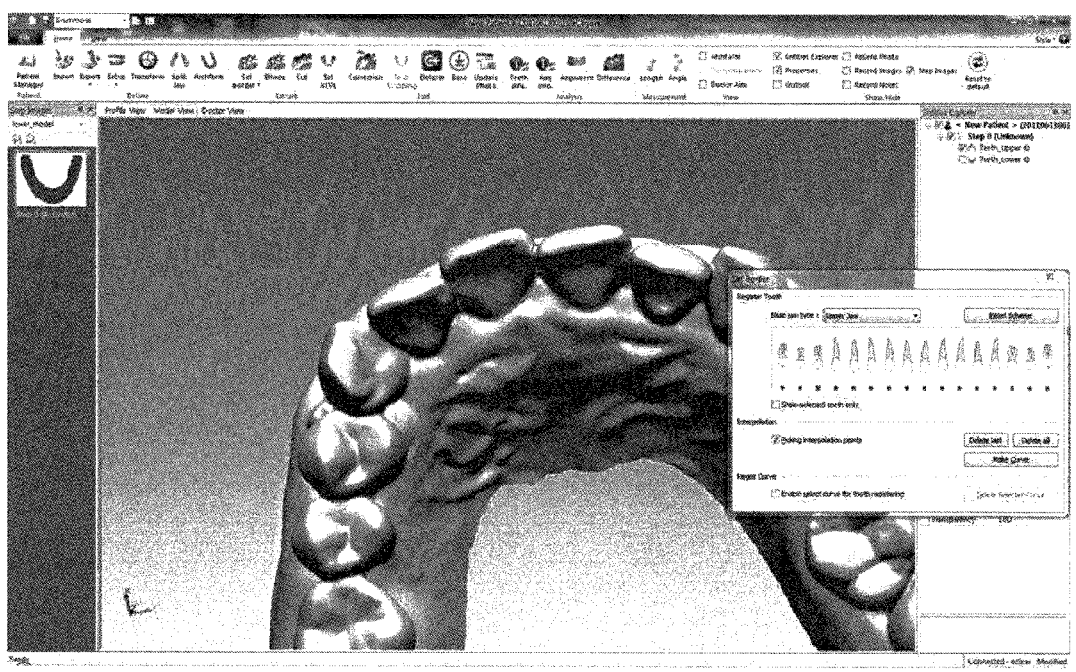

Since, in the 3D-scanned current dental data of the patient, the teeth and the gum area can be clearly separated from each other, the orthodontic module can easily separate the teeth and the gum area from each other by means of the image boundary detection or the selective designation, as shown in FIG. 7.

After the teeth are separated from the gum area, a tooth in need of orthodontia is separated from the other teeth.

Figure 8:
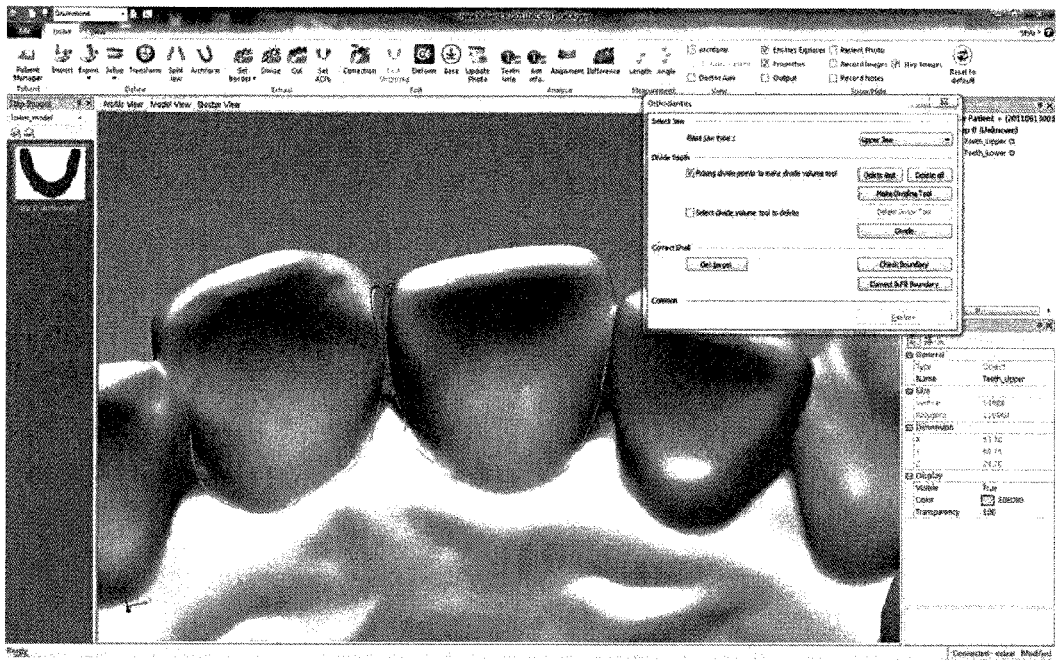
Figure 9:
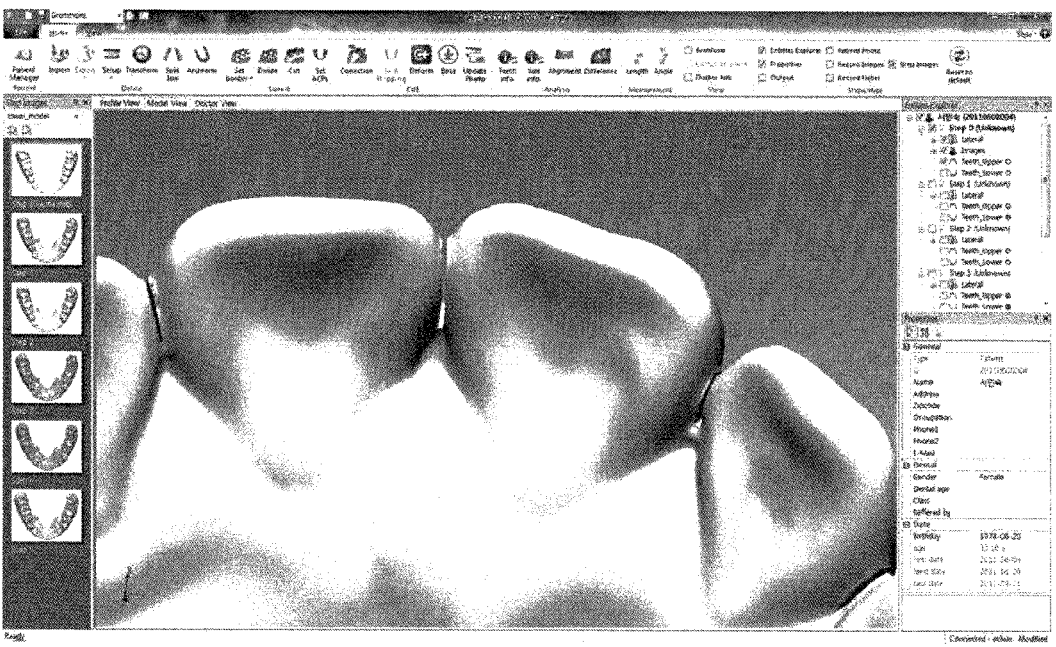

In the case of the teeth in need of orthodontia, the position of the teeth must be changed by expansion, rotation, and retraction operations. Therefore, space in which the teeth in need of orthodontia can move is required. In the scanned dental data, because the teeth may be excessively close to each other, it may difficult to distinguish the teeth from each other. Thus, as shown in FIGS. 8 and 9, it is required to separate teeth in need of orthodontia from the other teeth.

After the desired teeth are separated from the other teeth, reference information about each individual tooth is designated.

Figure 10:
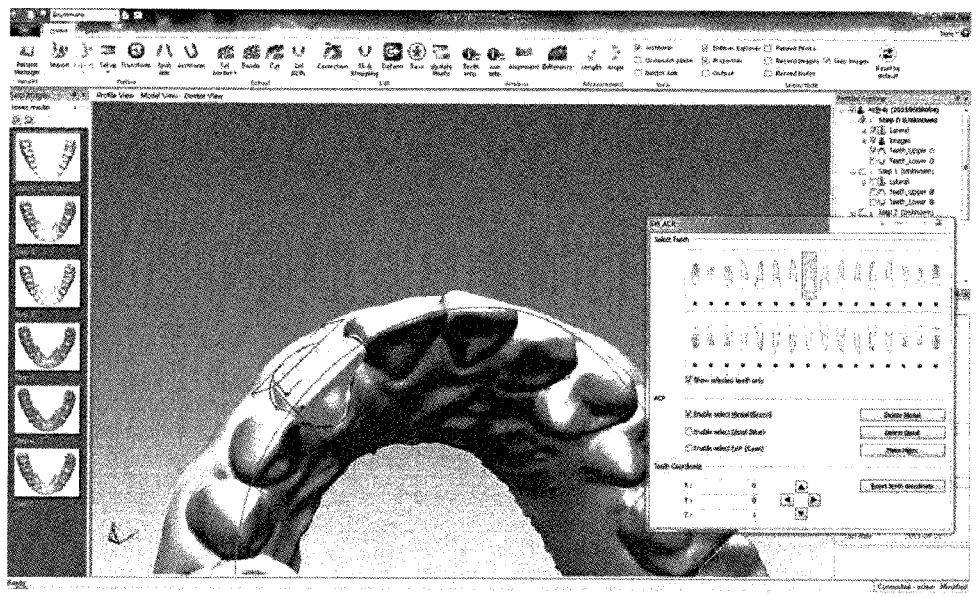

As shown in FIG. 10, the reference information includes information about a mesial point which is closest to the tongue based on an imaginary arch line formed in consideration of the whole of the teeth, a distal position which is furthest from the tongue, and a FAP point which is located at the center of teeth based on an imaginary arch line formed in consideration of the average height of the teeth.

Figure 11:
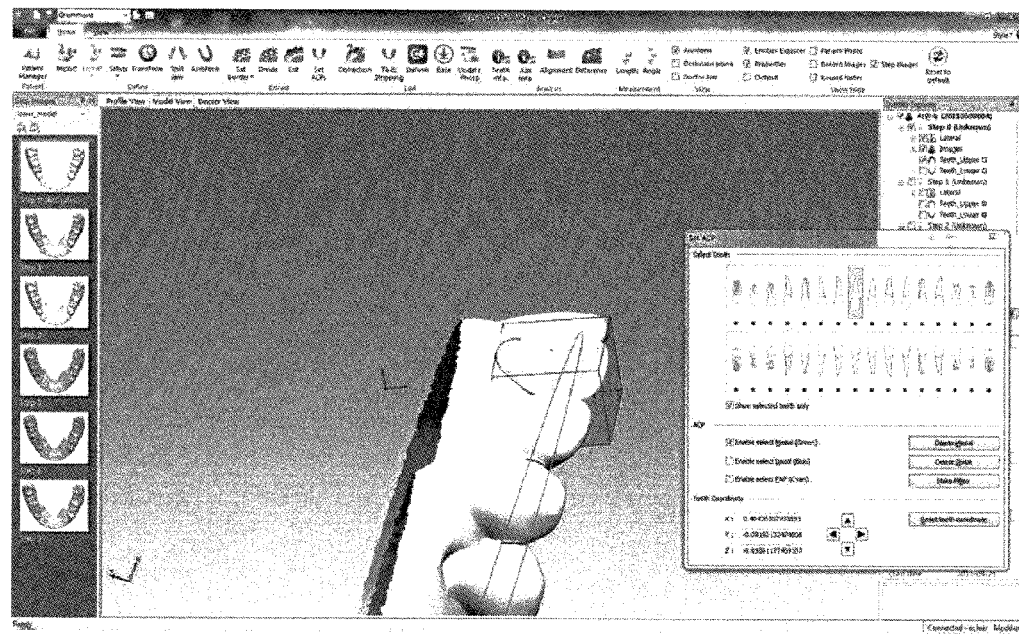

Further, as show in FIG. 11, the reference information includes information about an axis set to each tooth. In this way, the reference information is set. The reference information is applied to each tooth to map it with No. of each tooth.

As such, after the reference information of the teeth is set, displacement such as expansion, rotation and retraction of the teeth can be individually controlled.

Furthermore, after the reference information of the teeth is set, teeth in need of orthodontia are moved through expansion, rotation and retraction operations to create orthodontic dental data.

The orthodontic dental data is created by aligning the teeth to be in need of orthodontia with the imaginary arch line in such a way that the teeth are expanded, rotated or retracted based on the imaginary arch line formed when setting the reference information.

The orthodontic dental data is data created by moving the teeth in need of orthodontia to the desired positions through the expansion, rotation and retraction operations of the teeth. Because of restriction in the distance that the teeth can move, the final orthodontic dental data can be created through a plurality of steps.

Depending on conditions of teeth, the number of teeth in need of orthodontia, locations of the teeth, etc., the steps of the expansion, rotation and retraction operations of the teeth may be further subdivided. In the case of light orthodontia, the expansion, rotation and retraction operations may comprise comparatively few steps. As such, the number of steps of the operations required to create the final orthodontic dental data may vary depending on each characteristics of each patient.

The expansion of the tooth means protruding the tooth to secure space to rotate the tooth. The rotation of the tooth means moving the tooth in four directions, including up, down, left and right, towards the target orthodontic position. The retraction of the tooth means moving the tooth to its original position after the expanded tooth is corrected by the rotation.

Here, the expansion of the tooth is the operation which is required when space required for moving the tooth is not provided. If the space required for moving the tooth cannot be ensured by the expansion, a stripping operation in which the tooth is ground to reduce the width thereof may be further conducted.

Hereinafter, the method of creating the orthodontic dental data will be described in more detail with reference to the embodiment.

Figure 12:
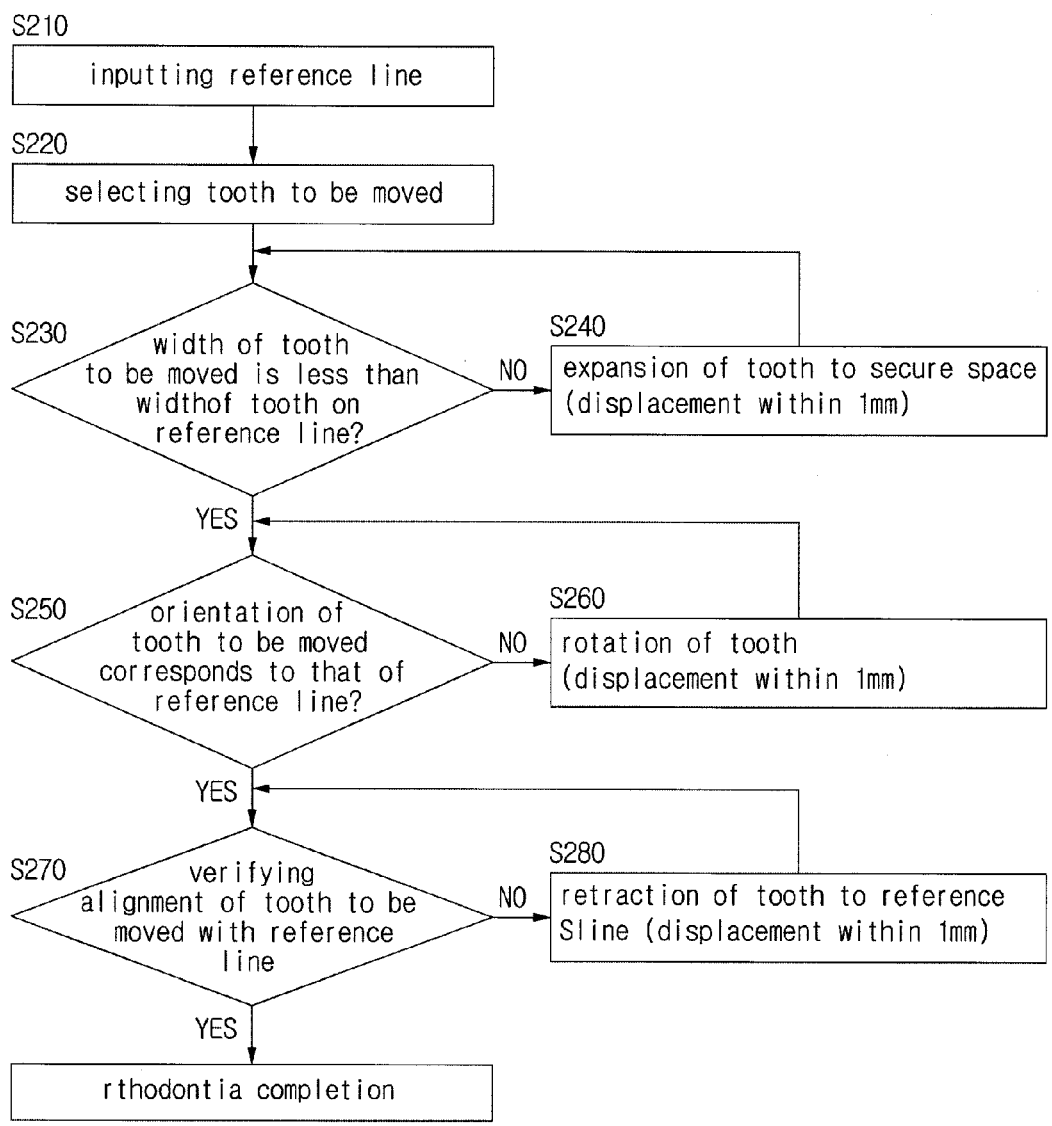
FIG. 12 is a flowchart of a method of creating orthodontic dental data according to the preferred embodiment of the present invention.

FIG. 12 is a flowchart of the method of creating orthodontic dental data according to the preferred embodiment of the present invention.

Figure 13:
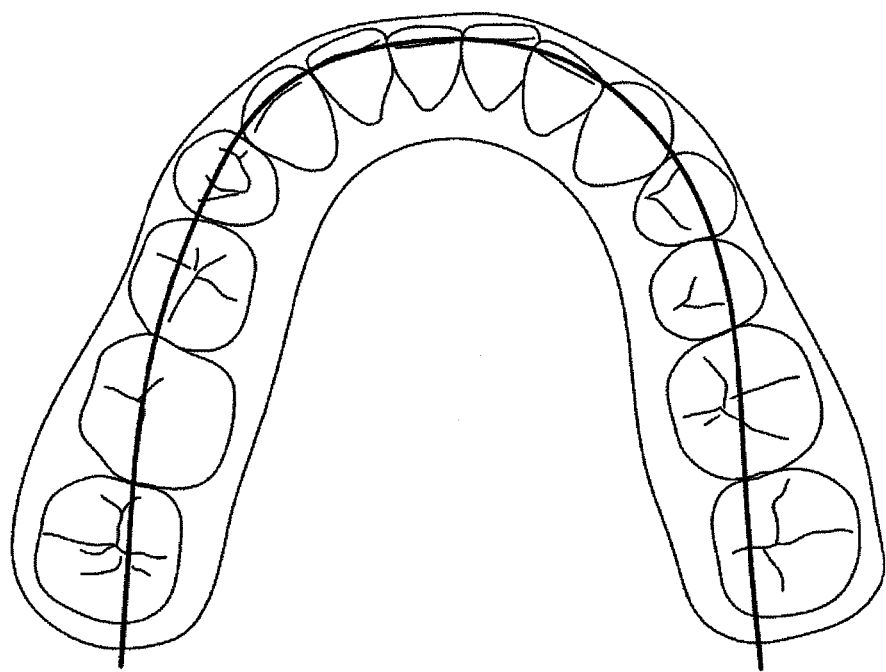
FIGS. 13 through 21 are views successively showing steps of the method of creating the orthodontic dental data of FIG. 12.

Referring to FIG. 12, a reference teeth line is applied to the teeth, as shown in FIG. 13, (at step S210).

The reference line is an arch line of ideal tooth arrangement.

Figure 14:
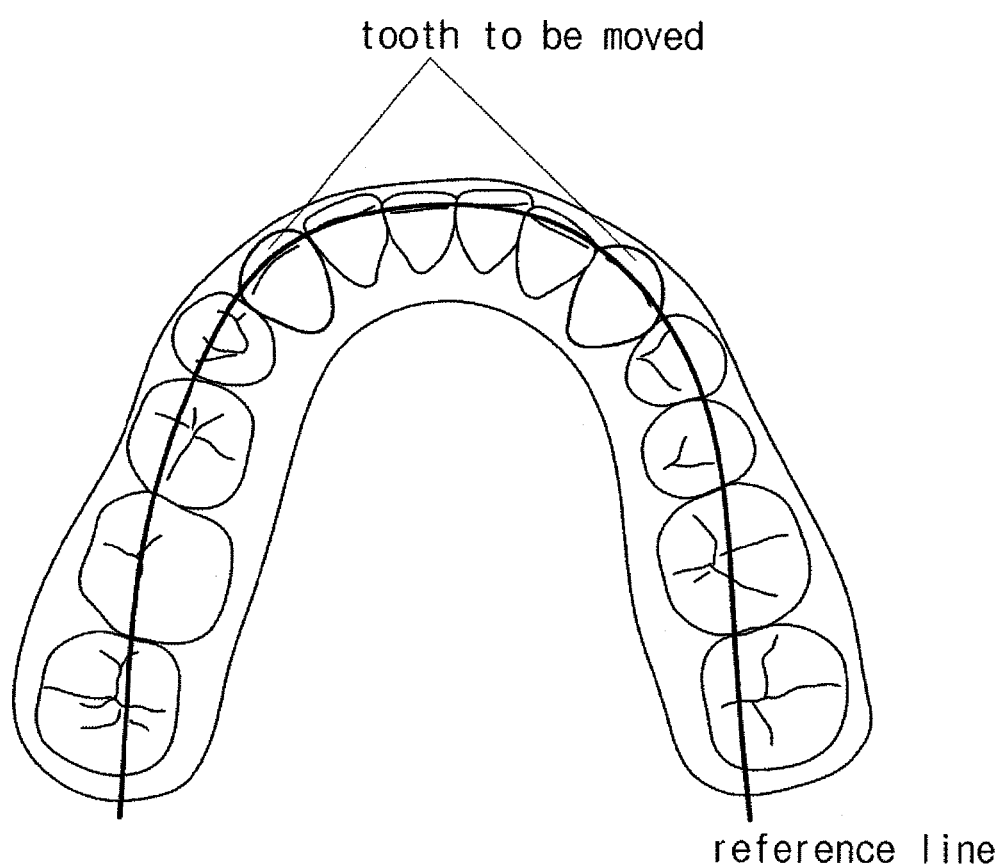

Thereafter, as shown in FIG. 14, teeth in need of movement are selected (at step S220).

The teeth in need of movement can be determined both from the degree with which a tooth is displaced from the reference line and from the degree with which a tooth is twisted around an axis thereof.

Figure 15:
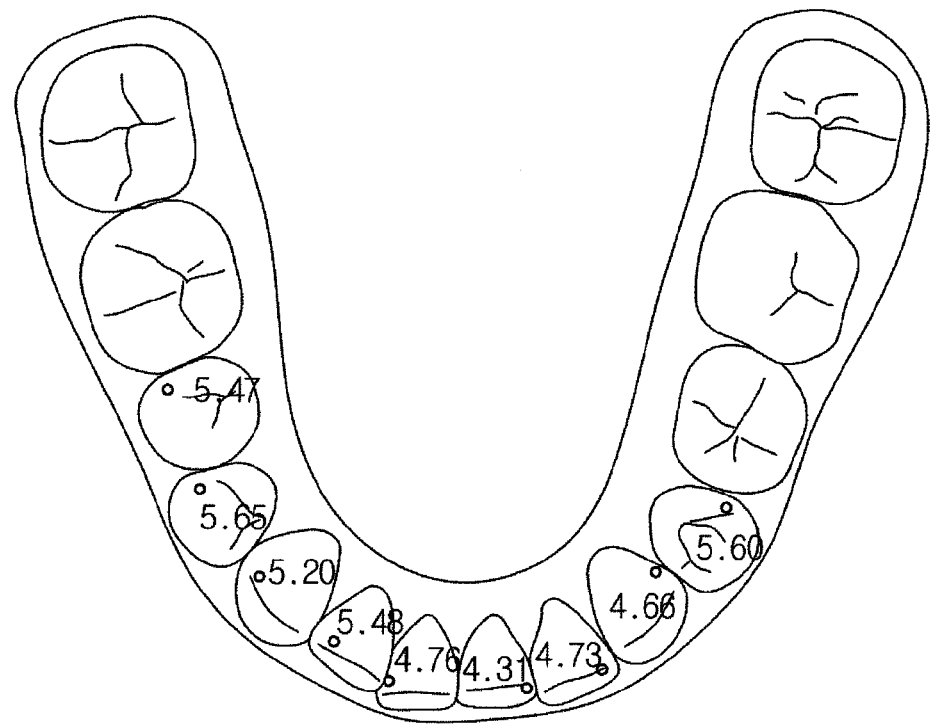

Subsequently, as shown in FIG. 15, the width of the teeth in need of movement is compared with the width of the reference line (at step S230).

In more detail, the teeth are separated, and the width of each tooth is measured using the mesial point and the distal point of the reference information.

After the width of each tooth is measured and the distance between teeth is determined, a securable width of the tooth based on the reference line is compared with the size of the tooth so as to determine whether space in which each tooth in need of movement can be moved is provided or not.

If the size of a tooth to be moved is greater than a reference tooth size based on the reference line, the tooth to be moved and teeth that are disposed on opposite sides thereof are expanded together so as to secure space (at step S240). In expansion of each tooth, a tooth movement distance at each time is limited to 1 mm or less.

The following Table 1 shows comparison of the actual width of each tooth with a securable width based on the reference line.

TABLE 1

| Tooth No. | 1 | 2 | 3 | 4 | 5 | 6 |
|---|---|---|---|---|---|---|
| Actual width | 5.20 | 5.48 | 4.76 | 4.31 | 4.73 | 4.66 |
| Securable width | 6.35 | 6.44 | 4.60 | 5.49 | 7.26 | 6.60 |

Figure 16:
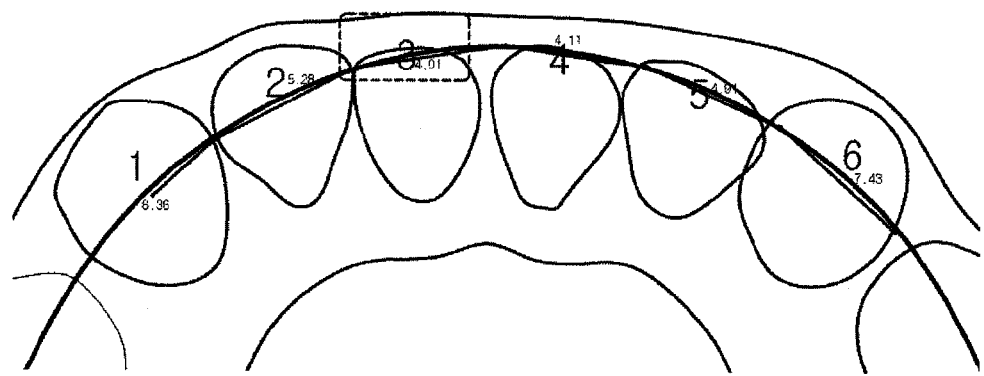
Figure 17:
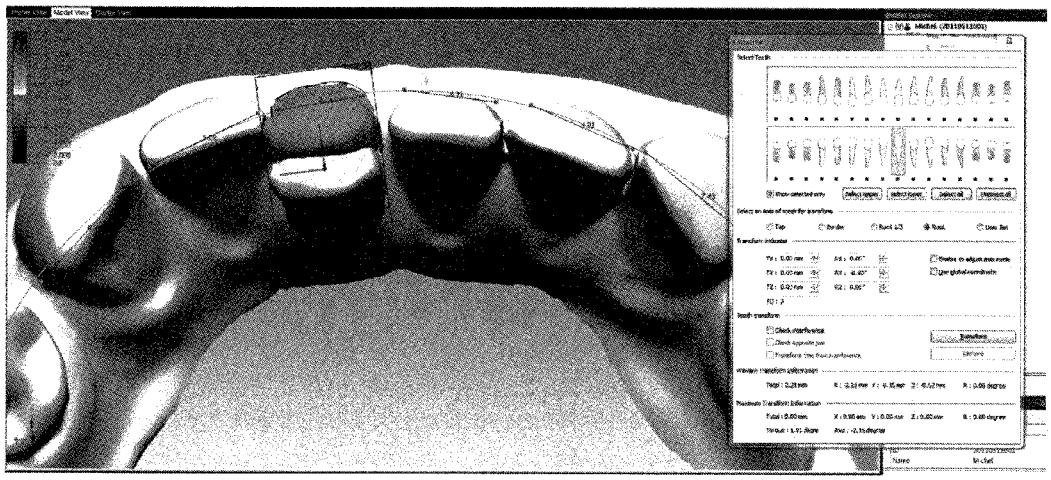
Figure 18:
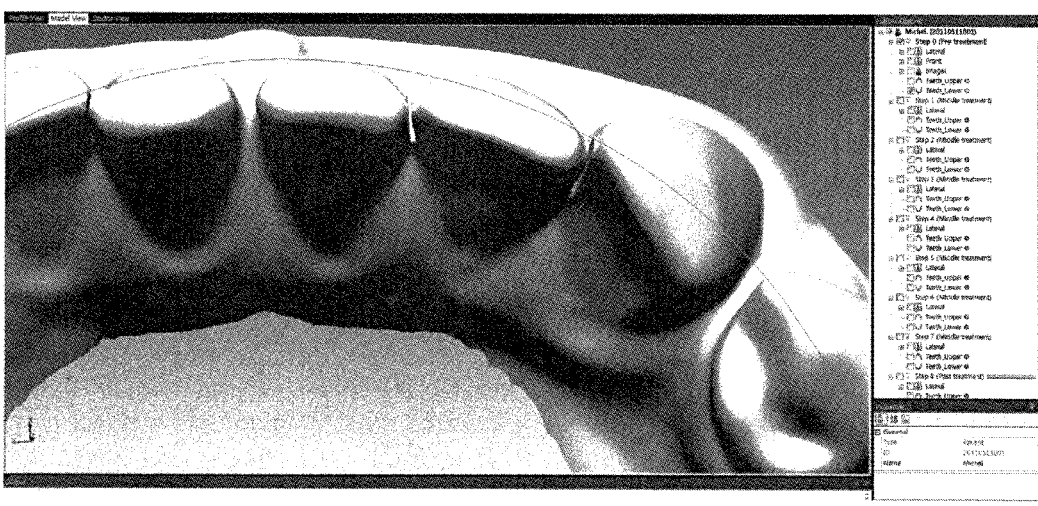

As can be understood from Table 1 and FIG. 16, in the case of tooth No. 3, because the actual width (4.76) of the tooth is greater than the securable width (4.6) based on the reference line, the expansion of the teeth is required. Thus, as shown in FIG. 17, the expansion is performed.

In some cases, if it is difficult to secure the space to move the tooth only using the expansion, the stripping operation for reducing the width of the corresponding tooth to secure the space may be performed.

After the expansion operation is conducted, whether the width of the tooth to be moved is less than the securable width based on the reference line so as to secure the space to move the tooth is determined again. If the space is not secured, step S240 is repeated.

In the case where the width of the tooth to be moved is less than the securable width based on the reference line so that the space is secured, the expansion operation may be omitted. Thereafter, whether the orientation of the tooth to be moved corresponds to that of the reference line is determined (at step S250).

Figure 19:
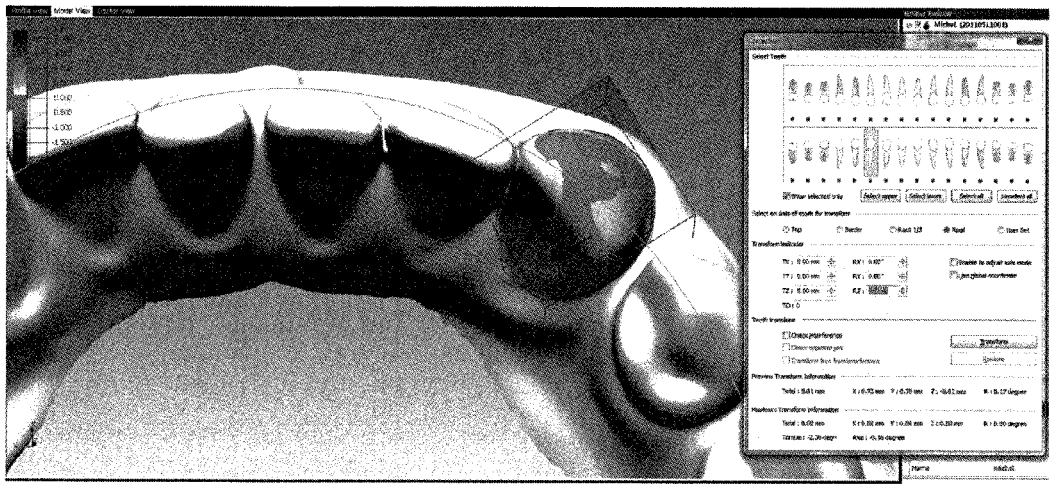

If the orientation of the tooth to be moved does not correspond to that of the reference line, the tooth is rotated based on the FAP point, as shown in FIG. 19 (at step S260). The displacement of the rotation of the tooth at each time is limited to 1 mm or less.

Figure 20:
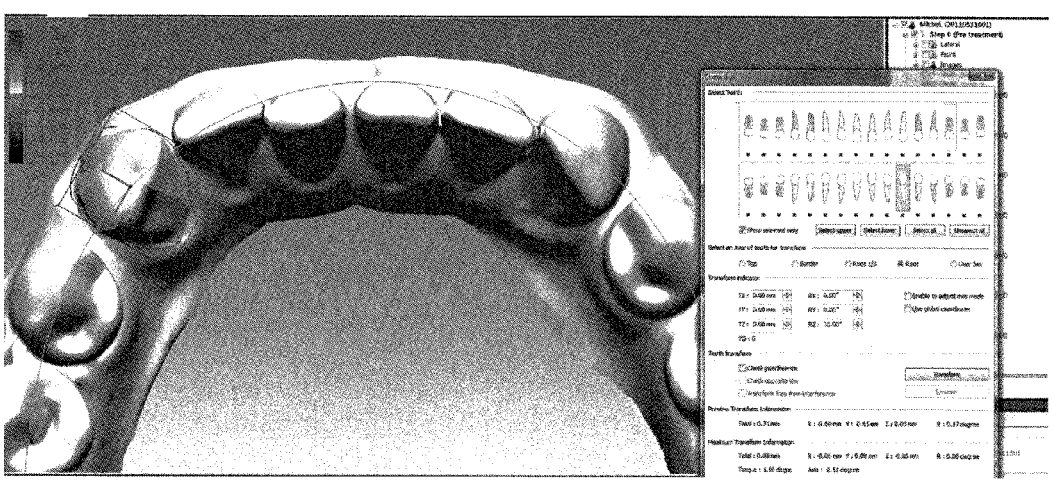

After the rotation operation has been completed, whether the orientation of the tooth to be moved corresponds to that of the reference line is determined again. If, as shown in FIG. 20, they do not correspond to each other, step S260 is repeated.

If the orientation of the tooth to be moved corresponds to that of the reference line through the rotation operation, the tooth to be moved is aligned with the reference line (at step S270).

If, after the rotation operation has been completed, the tooth to be moved is not aligned with the reference line, the retraction operation of the tooth is conducted (at step S280). In the retraction operation, the displacement of the tooth at each time is limited to 1 mm or less.

Figure 21:
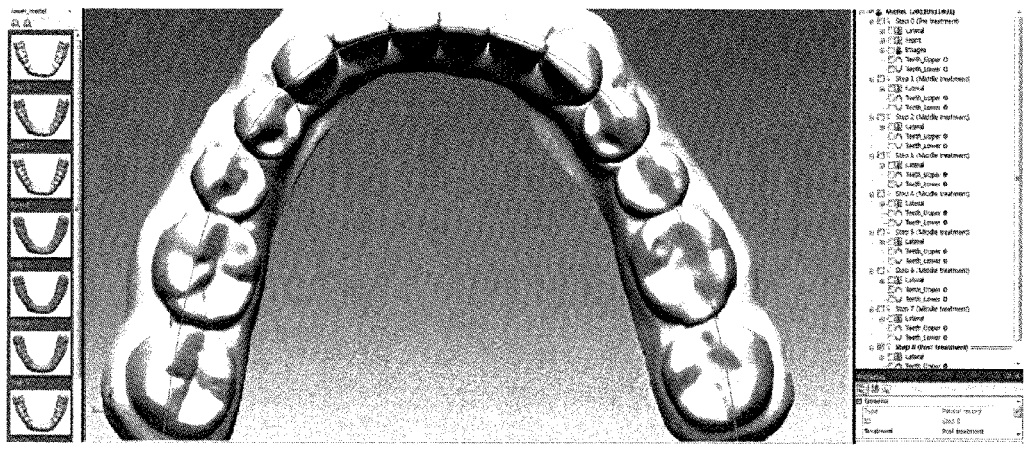

Subsequently, whether the tooth to be moved is aligned with the reference line is determined again, and if it is not aligned, step S280 is repeated. If it is aligned, the orthodontia process is completed, as shown in FIG. 21.

FIGS. 22 through 30 are views successively showing the several steps of the process of creating the orthodontic dental data according to the embodiment of the present invention.

Figure 22:
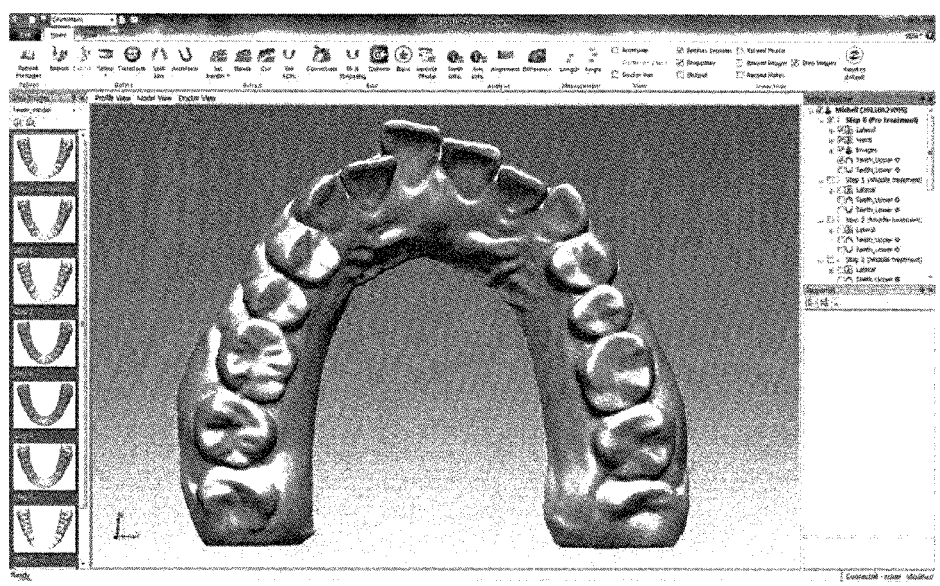
FIGS. 22 through 30 are views successively showing steps of a process of creating the orthodontic dental data according to the embodiment of the present invention.

Referring to FIGS. 22 through 30, in this embodiment, the orthodontic dental data is created from the current dental data through a total of seven steps. FIG. 22 illustrates the current dental data before the orthodontia process.

Figure 23:
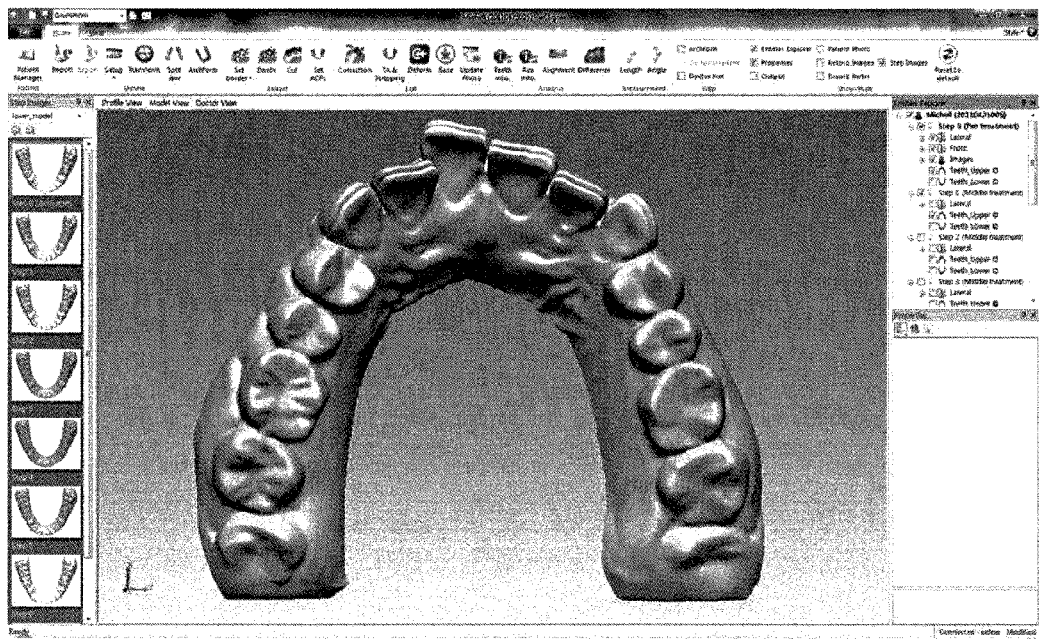
Figure 24:
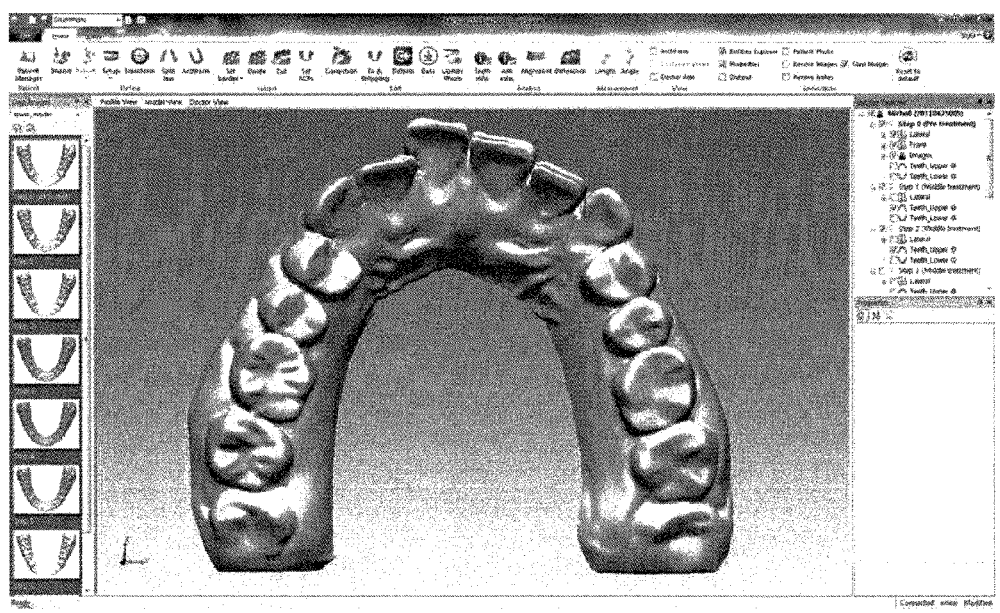
Figure 25:
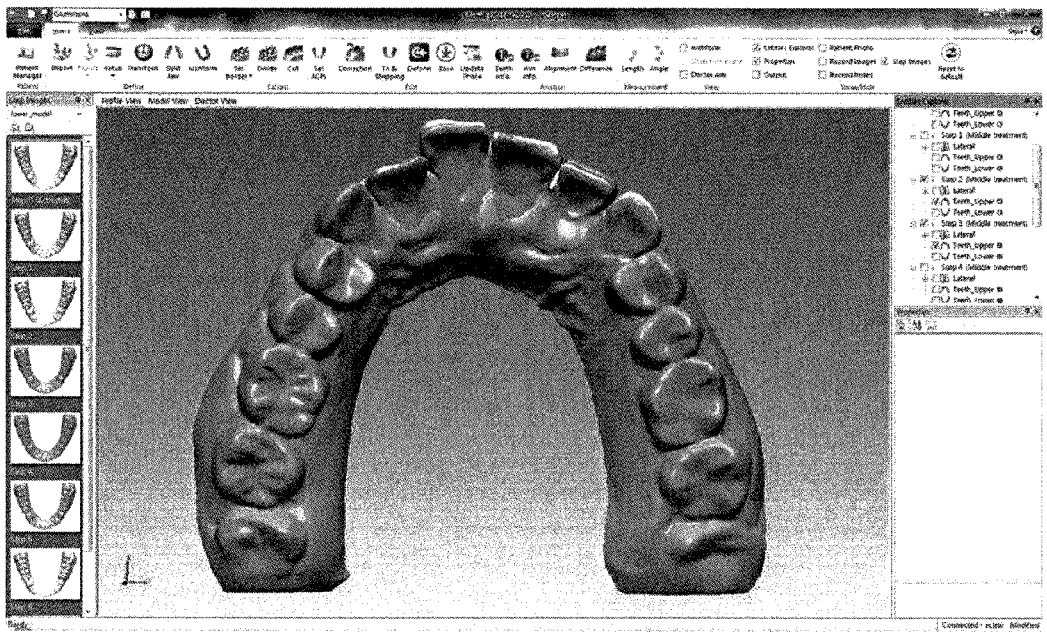

FIGS. 23 through 25 illustrate the first through third steps of the orthodontia process, in detail, showing the orthodontic dental data in the steps of the expansion operation to rotate the tooth.

The reason why the expansion operation is divided into three steps is the fact that because the distance that the tooth can be moved at each step is limited, if the distance that the tooth must be moved during the expansion operation is comparatively long, the expansion operation must be divided into a plurality of steps.

Figure 26:
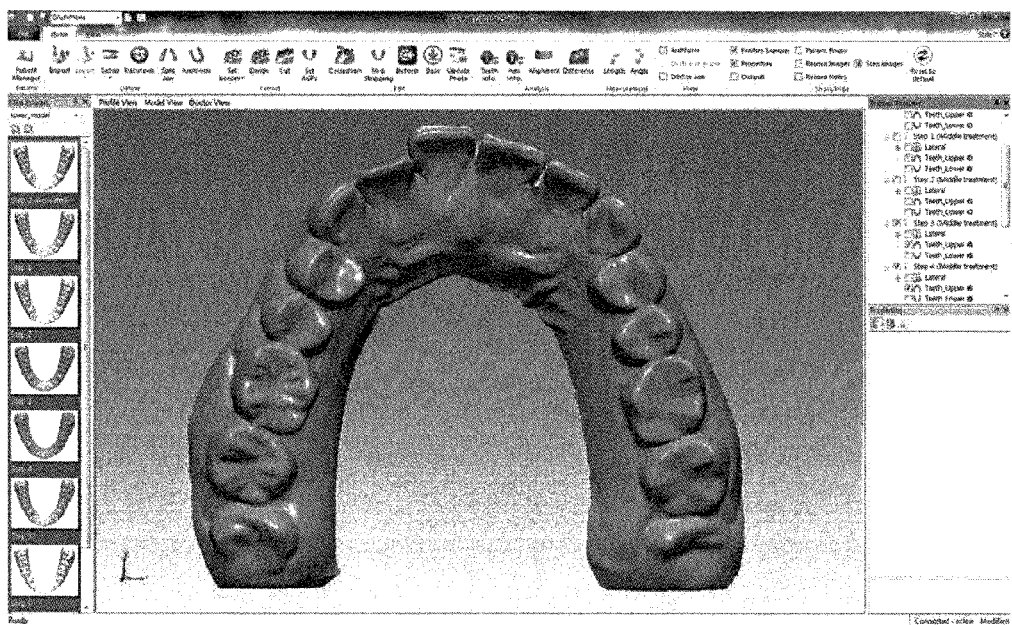

FIG. 26 illustrates the fourth step, that is, showing the orthodontic dental data which is in the step of rotating the expanded tooth.

Figure 27:
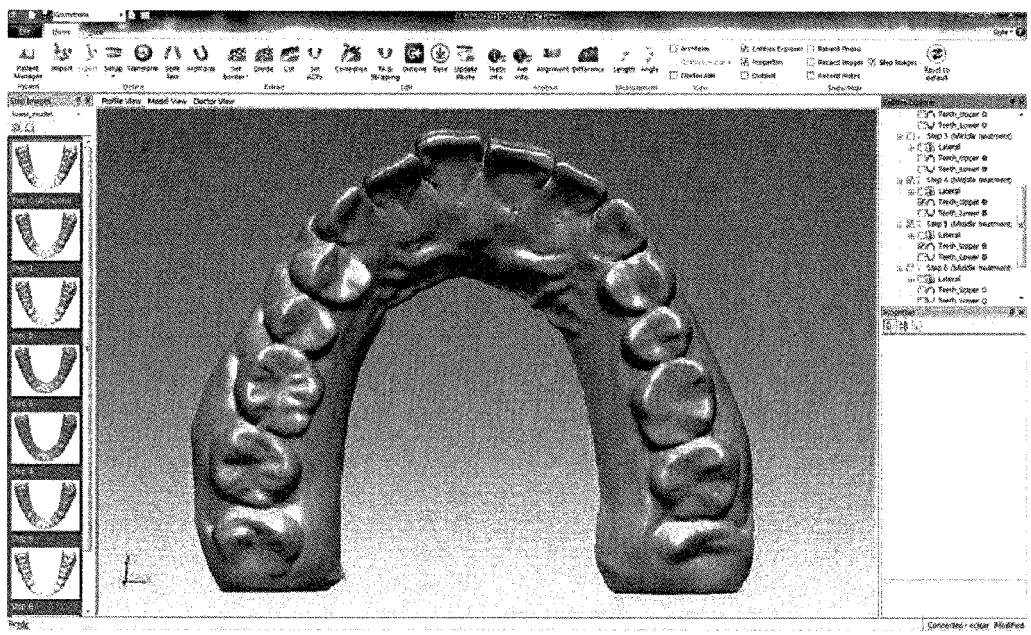
Figure 28:
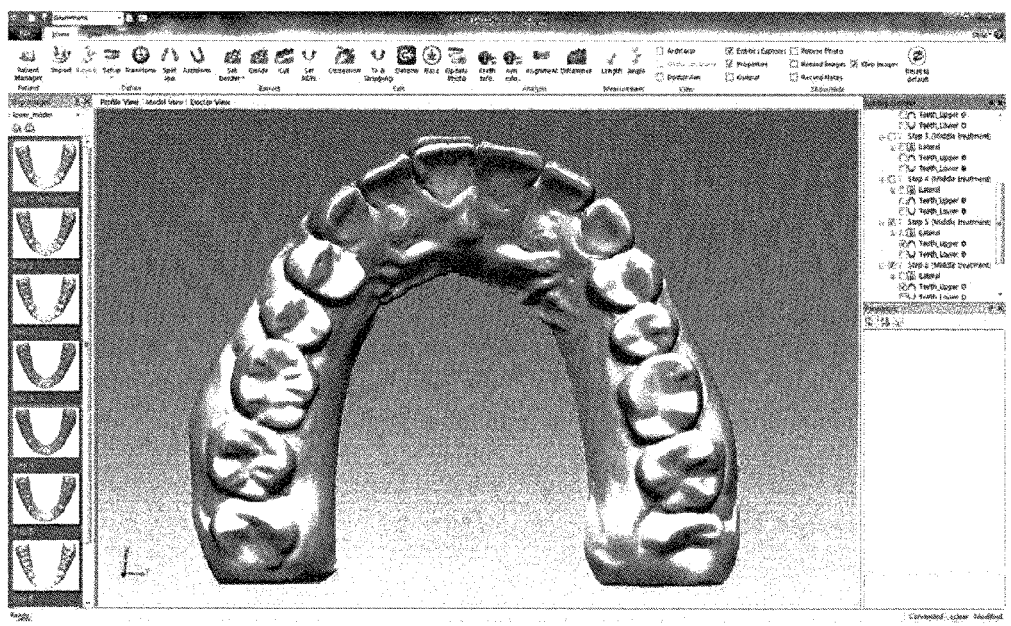
Figure 29:
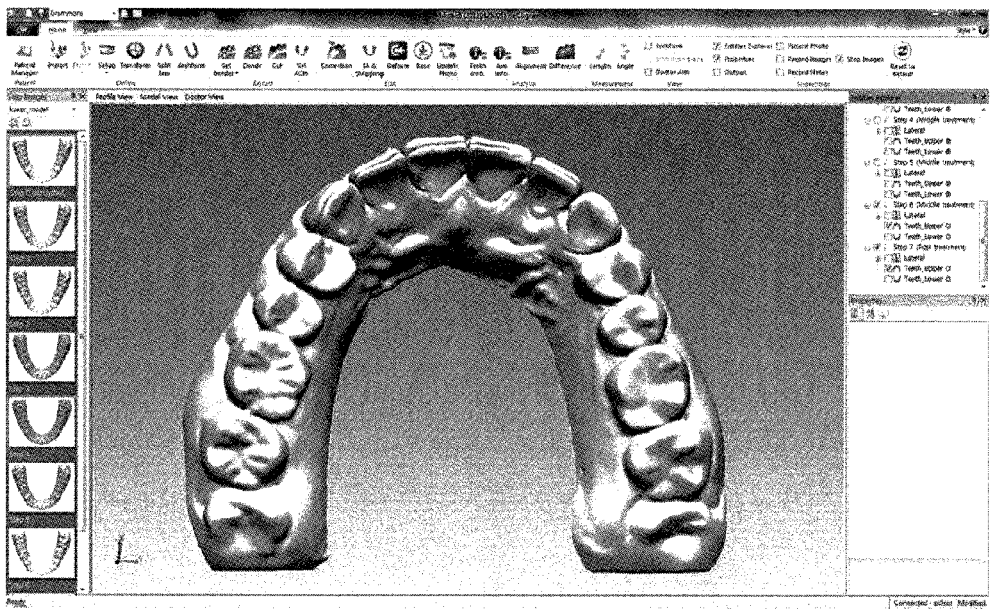

FIGS. 27 through 29 illustrate the fifth through seventh steps of the orthodontia process, in detail, showing the orthodontic dental data in the steps of retracting the rotated tooth to its original position. The orthodontic dental data of the seventh step becomes the final orthodontic dental data.

Figure 30:
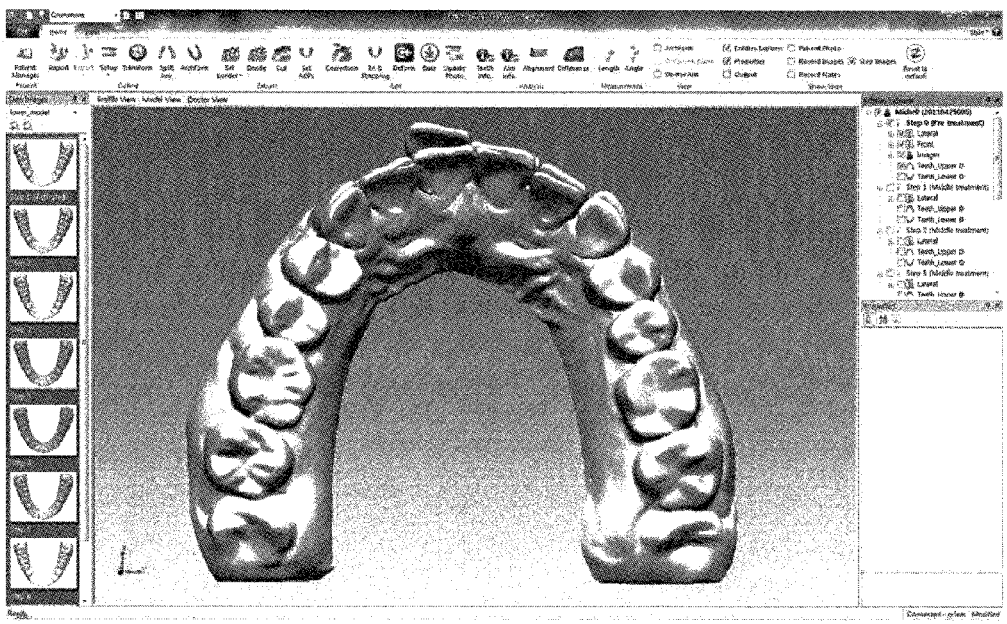

FIG. 30 compares the current dental data before the orthodontia with the final orthodontic dental data after the orthodontia.

After the final orthodontic dental data is created, the simulation unit creates data for comparing variation in the face contour of the patient before and after the orthodontia (at step S150).

Figure 31:
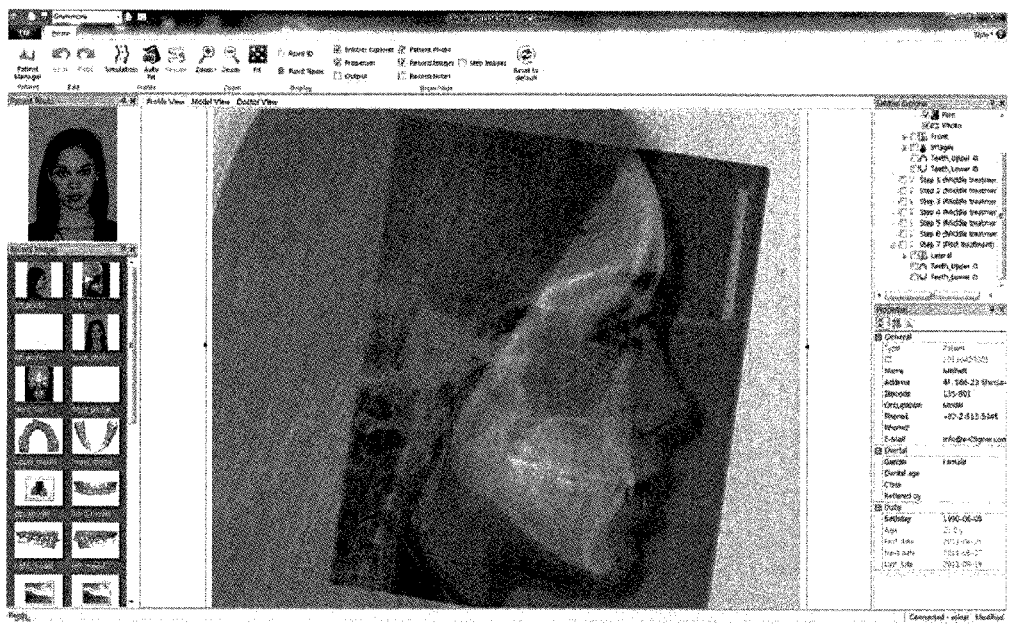
FIGS. 31 through 33 are views successively showing steps of a process of creating data for comparing the appearance variation of a patient pre-orthodontia and post-orthodontia according to the embodiment of the present invention.
Figure 32:
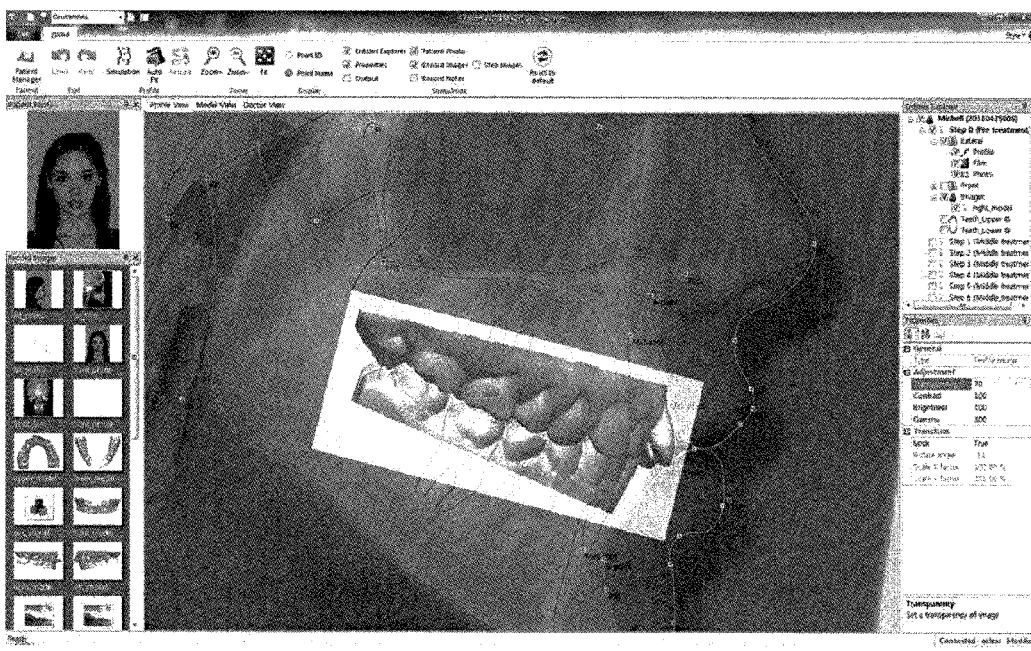

In detail, as shown in FIG. 31, after overlapping the side face photograph of the patient with the X-ray photograph, profile information in which reference points of the craniofacial skeleton are connected to each other is created. Thereafter, as shown in FIG. 32, the current dental data is mapped with the profile information.

Figure 33:

In the pre-orthodontia data in which the side face photograph, the X-ray photograph and the current dental data of the patient are mapped, the current dental data is changed to the orthodontic dental data. Then, as shown in FIG. 33, orthodontic data which shows a changed face contour of the patient is created.

Figure 34:
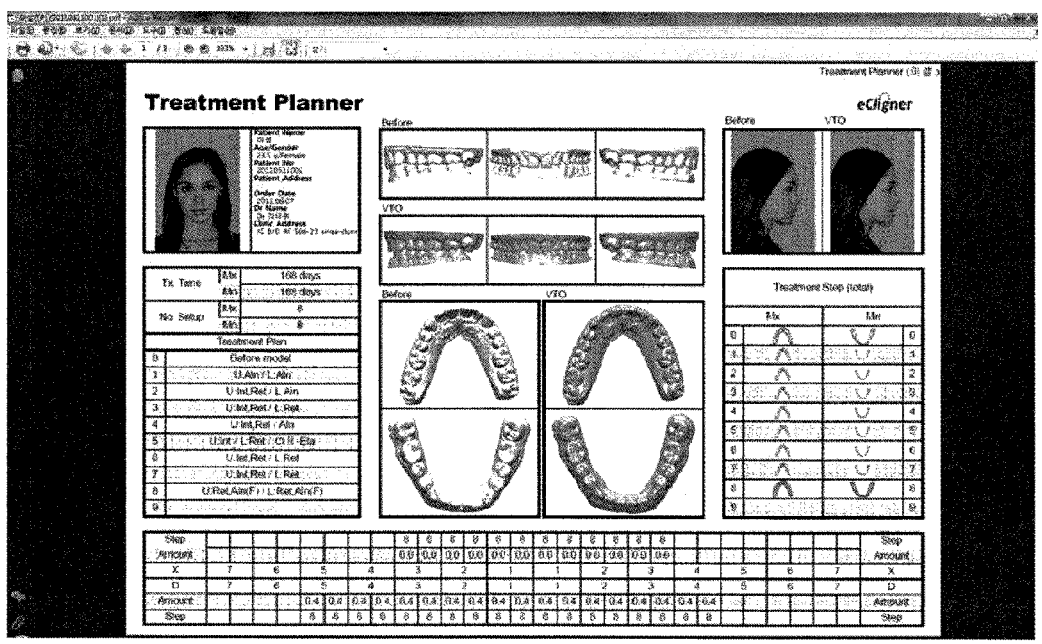
FIG. 34 is a view schematically showing an orthodontic dental data format according to the embodiment of the present invention.

As such, after the simulation unit creates comparison data between pre-orthodontia and post-orthodontia, as shown in FIG. 34, the orthodontic data which includes the comparison data between pre-orthodontia and post-orthodontia and the orthodontic dental data is transmitted to the dental terminal that has asked orthodontia, and the dentist and the patient check the orthodontic data (at step S160).

If there are correction details of the orthodontic data, the dentist can request correction details of the orthodontia through the dental terminal (at step S170). In this case, the process feeds back to step S140.

When the orthodontic data is finally decided, dental molds for respective steps of the orthodontic dental data are manufactured (at step S180).

In this embodiment, the orthodontic dental data of the seven steps are created. In this case, on the basis of the seven kinds of orthodontic dental data, dental molds are manufactured by means of the 3D printer.

Here, a plurality of dental molds are manufactured for each patient. Dental molds for several patients may be manufactured at the same time. Thus, after 3D printing, the manufactured dental molds for several patients may be mixed with each other.

To prevent such a problem, it is preferable that before 3D printing, information for identifying a dental mold to be manufactured be input to the orthodontic dental data such that it is expressed in an engraving manner.

Figure 35:
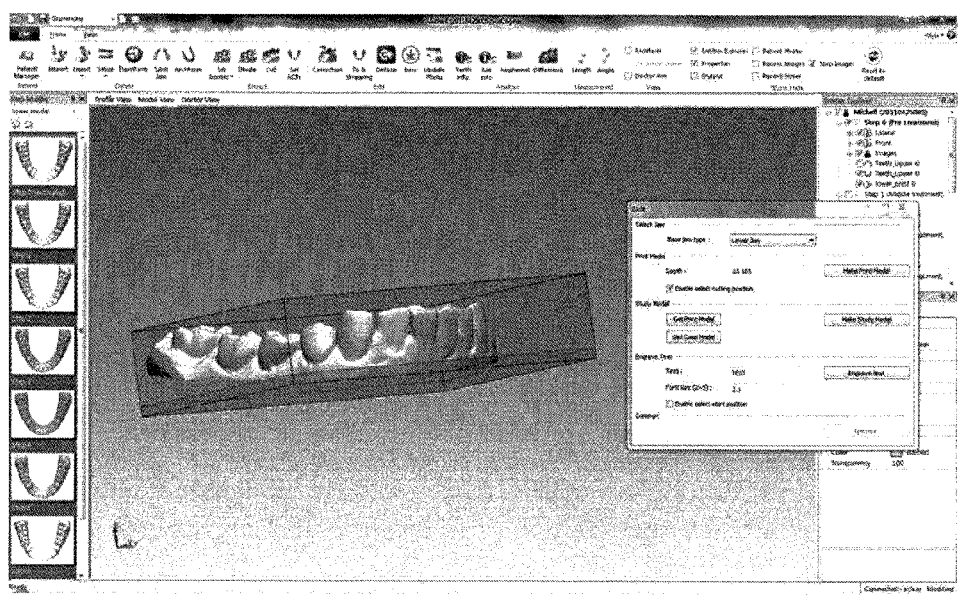
FIGS. 35 to 37 are views successively showing steps of a process of applying identification information to a dental mold according to the embodiment of the present invention.
Figure 36:
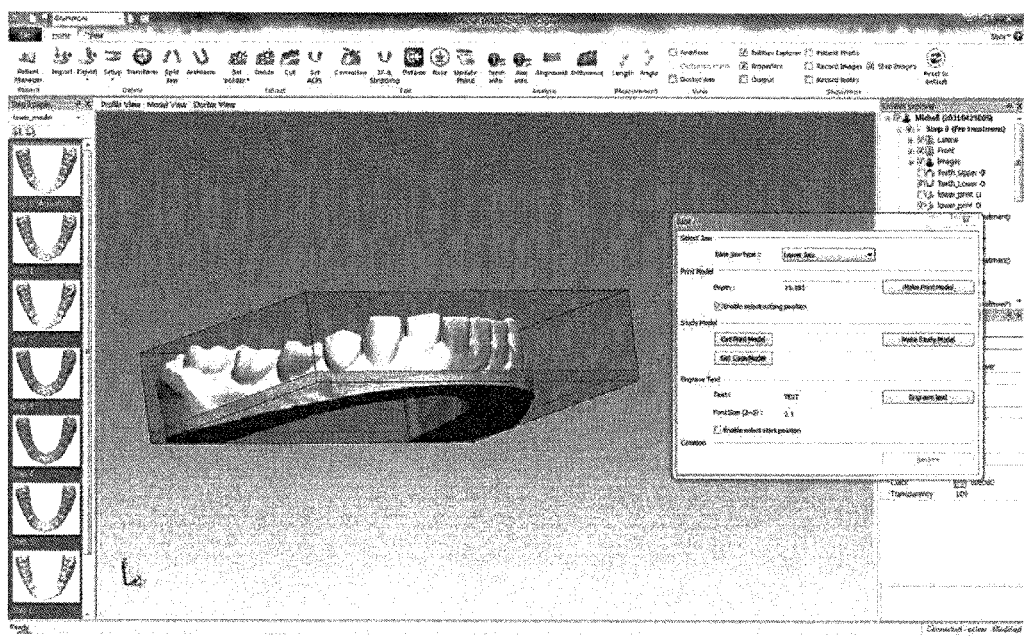
Figure 37:
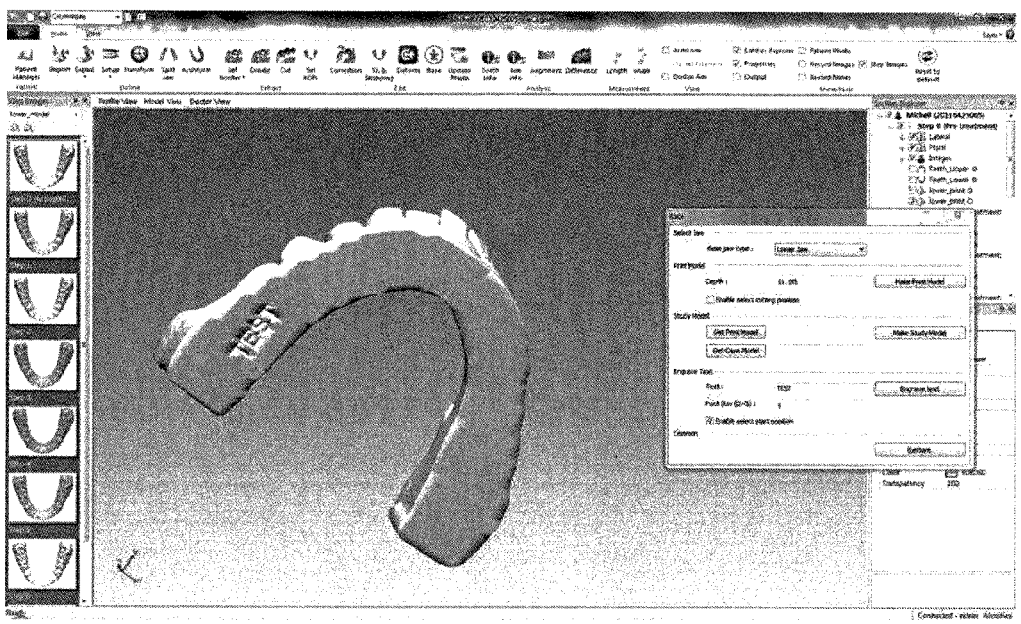

In more detail, with regard to orthodontic dental data, as shown in FIGS. 35 and 36, a bottom area of the gum is formed in a planar shape, and as shown in FIG. 37, dental mold identification information is applied to the bottom surface in an engraving manner.

The dental mold identification information is information for identifying a dental mold, including the name of a patient, information about the step of the orthodontic dental data, etc.

As such, if the identification information is input, it is printed in the bottom of the dental mold manufactured by the 3D printer in an engraving manner.

After the dental molds with regard to the respective steps of the process are completed, a transparent brace for each step is manufactured in such a way that a transparent substance is vacuum-pressed onto the dental mold for each step by means of the vacuum compressor (at step S190).

If the transparent brace is made of high-solidity material, it may not be easily compatible with the teeth of the patient. Therefore, when the transparent brace for each step is manufactured, it is preferable that a plurality of transparent braces that have different rigidities be manufactured.

In more detail, Tupan which is transparent material varies in rigidity depending on the thickness thereof in such a way that as the thickness thereof is reduced, the rigidity thereof is also reduced. Given this, several transparent braces are manufactured such that the thicknesses of them are successively increased by steps.

For instance, the rigidities of the transparent braces are classified into three types including a soft type, a medium type and a hard type according to the thickness. By steps, the patient wears the transparent braces in a sequence of the soft type, the medium type and the hard type so as to minimize discomfort and enhance compatibility with his or her teeth. In addition, because the duration for which the patient wears each transparent brace is reduced, there are advantages in terms of hygiene.

Although the preferred embodiment of the present invention has been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described above, in the present invention, a plurality of steps of orthodontic dental data are created to form a final orthodontic dental data on the basis of individual movement of teeth, so that more accurate orthodontia is possible. Therefore, the present invention is very useful for transparent brace production industry.

The invention claimed is:

1. A method for manufacturing a transparent brace, comprising:
    receiving dental data of a patient transmitted from a dental terminal;
    preprocessing data about a 3D-scanned dental model and creating current dental data of the patient;
    processing the current dental data through an orthodontia process and creating multi-step orthodontic dental data using an orthodontic module;
    manufacturing a plurality of multi-step dental molds through 3D printing based on the multi-step orthodontic dental data; and
    manufacturing a plurality of multi-step transparent braces in such a way transparent substances are vacuum-pressed onto the multi-step dental molds, respectively,
    wherein creating the multi-step orthodontic dental data comprises:
        dividing teeth of the patient into upper jaw teeth and lower jaw teeth;
        positioning the current dental data for orthodontia;
        separating the teeth from a gum area;
        separating the teeth from each other to secure space for moving a tooth;

setting reference teeth information;
processing the tooth based on the set reference teeth information through at least one of an expansion operation, a rotation operation and a retraction operation and creating the multi-step orthodontic dental data; and
performing a stripping operation of grinding the tooth to reduce a width of the tooth when the space to move the tooth is not secured by the expansion operation of the tooth,
wherein the orthodontic module creates the multi-step orthodontic dental data in accordance with the expansion operation, the rotation operation and the retraction operation of the tooth such that a distance that the tooth moves at each step is within a range of 1 mm or less.

2. The method of claim 1, after creating the orthodontic dental data, further comprising:
creating pre-orthodontia and post-orthodontia data so that variation in a face contour of the patient based on the current dental data and the orthodontic dental data can be checked; and
verifying the pre-orthodontia and post-orthodontia data and the orthodontic dental data.

3. The method of claim 1, wherein preprocessing the 3D-scanned dental model data comprises automatically setting a resolution and a size of the 3D-scanned data to a preset format.

4. The method of claim 1, wherein the orthodontic module determines a tooth in need of orthodontia depending on a degree with which the tooth is displaced from a reference line (an imaginary arch line), and processes the tooth through the expansion operation, the rotation operation and the retraction operation such that the tooth is aligned with the reference line, thus creating step orthodontic data.

5. The method of claim 2, wherein creating the pre-orthodontia and post-orthodontia data comprises:
overlapping a side face photograph of the dental data of the patient with an X-ray photograph of the face of the patient;
creating profile information in which reference points of a craniofacial skeleton of the patient are connected to each other while the side face photograph overlaps with the X-ray photograph, and mapping the current dental data with the profile information;
changing, from the pre-orthodontia data in which the side face photograph, the X-ray photograph and the current dental data of the patient are mapped with each other, the current dental data to the processed orthodontic dental data; and
creating the post-orthodontia data in such a way that, in response to a displacement resulting from the change of the current dental data to the orthodontic dental data, the X-ray photograph and the side face photograph that are integrally mapped with each other are varied by the displacement.

6. The method of claim 2, wherein verifying the pre-orthodontia and post-orthodontia data comprises:
transmitting orthodontic data including both the created orthodontic dental data and the pre-orthodontia and post-orthodontia data to the dental terminal, and allowing a dentist and the patient to verify the orthodontic data;
filing correction details of the orthodontic data to an orthodontic management server, the dentist determining whether the correction details are present; and
feeding back to creating the orthodontic dental data when the correction details are received.

7. The method of claim 1, wherein manufacturing the plurality of multi-step dental molds comprises inputting dental mold identification information to the multi-step orthodontic dental data so that the dental mold identification information is formed in bottom surfaces of the dental molds in an engraving manner.

8. The method of claim 1, wherein manufacturing the plurality of multi-step transparent braces comprises vacuum-pressing transparent substances having different thicknesses onto the plurality of multi-step dental molds, respectively, and manufacturing the plurality of multi-step transparent braces having different rigidities.

9. A method for manufacturing a transparent brace, comprising:
receiving dental data of a patient transmitted from a dental terminal;
preprocessing data about a 3D-scanned dental model and creating current dental data of the patient;
processing the current dental data through an orthodontia process and creating multi-step orthodontic dental data using an orthodontic module;
manufacturing a plurality of multi-step dental molds through 3D printing based on the multi-step orthodontic dental data;
manufacturing a plurality of multi-step transparent braces in such a way transparent substances are vacuum-pressed onto the multi-step dental molds, respectively;
creating pre-orthodontia and post-orthodontia data so that variation in a face contour of the patient based on the current dental data and the orthodontic dental data can be checked; and
verifying the pre-orthodontia and post-orthodontia data and the orthodontic dental data,
wherein creating the pre-orthodontia and post-orthodontia data comprises:
overlapping a side face photograph of the dental data of the patient with an X-ray photograph of the face of the patient;
creating profile information in which reference points of a craniofacial skeleton of the patient are connected to each other while the side face photograph overlaps with the X-ray photograph, and mapping the current dental data with the profile information;
changing, from the pre-orthodontia data in which the side face photograph, the X-ray photograph and the current dental data of the patient are mapped with each other, the current dental data to the processed orthodontic dental data; and
creating the post-orthodontia data in such a way that, in response to a displacement resulting from the change of the current dental data to the orthodontic dental data, the X-ray photograph and the side face photograph that are integrally mapped with each other are varied by the displacement.

* * * * *